(12) United States Patent
Sadasivan et al.

(10) Patent No.: US 9,504,588 B2
(45) Date of Patent: Nov. 29, 2016

(54) SYSTEM AND METHOD FOR SIMULATING DEPLOYMENT CONFIGURATION OF AN EXPANDABLE DEVICE

(75) Inventors: Chandramouli Sadasivan, Port Jefferson, NY (US); Baruch Barry Lieber, South Setauket, NY (US); David Fiorella, East Setauket, NY (US); Henry Woo, Setauket, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 444 days.

(21) Appl. No.: 13/489,436

(22) Filed: Jun. 5, 2012

(65) Prior Publication Data

US 2012/0310611 A1    Dec. 6, 2012

Related U.S. Application Data

(60) Provisional application No. 61/493,513, filed on Jun. 5, 2011, provisional application No. 61/493,976, filed on Jun. 6, 2011.

(51) Int. Cl.
| | |
|---|---|
| *A61F 2/90* | (2013.01) |
| *A61F 2/88* | (2006.01) |
| *G06F 19/00* | (2011.01) |
| *A61F 2/82* | (2013.01) |
| *G06F 17/50* | (2006.01) |
| *D04C 1/06* | (2006.01) |

(52) U.S. Cl.
CPC . *A61F 2/90* (2013.01); *D04C 1/06* (2013.01); *A61F 2/88* (2013.01); *A61F 2/885* (2013.01); *A61F 2002/823* (2013.01); *D10B 2509/06* (2013.01); *G06F 17/5009* (2013.01); *G06F 19/3437* (2013.01)

(58) Field of Classification Search
None
See application file for complete search history.

(56) References Cited

U.S. PATENT DOCUMENTS

| | | | |
|---|---|---|---|
| 6,273,895 B1 * | 8/2001 | Pinchuk et al. | .............. 606/108 |
| 6,501,848 B1 | 12/2002 | Carroll et al. | |
| 7,356,367 B2 | 4/2008 | Liang et al. | |

(Continued)

OTHER PUBLICATIONS

M. Jedwab, et al, "A Study of the Geometrical and Mechanical Properties of a Self Expanding Metallic Stent Theory and Experiment," Journal of Applied Biomaterials, vol. 4, 1993, pp. 77-85.*

(Continued)

*Primary Examiner* — Aniss Chad
*Assistant Examiner* — David M Rogers
(74) *Attorney, Agent, or Firm* — Fox Rothschild LLP

(57) ABSTRACT

A system, method, computer-readable medium, apparatus, and device for simulating placement of an expandable device in a cavity is provided. For example, a three or more dimensional image of a cavity, e.g., a tubular cavity, geometry is acquired. A centerline of the cavity, and a perimeter of the cavity based on the centerline of the cavity and the three-dimensional image of the cavity geometry, are determined. The length of a wire of the expandable device as the wire rotates along the perimeter of the cavity in a deployment direction is determined. A pitch of the rotation of the wire based on a local diameter at the centerline site of rotation and in-air parameters of the expandable device is determined. A deployed device length of the expandable device along the centerline of the cavity is determined. A processor is usable to determine and/or calculate each of the above.

39 Claims, 4 Drawing Sheets

(56) References Cited

U.S. PATENT DOCUMENTS

| | | | |
|---|---|---|---|
| 7,371,067 B2 | 5/2008 | Anderson et al. | |
| 7,650,179 B2 | 1/2010 | Redel et al. | |
| 7,873,194 B2 | 1/2011 | Begelman | |
| 7,930,014 B2 | 4/2011 | Huennekens et al. | |
| 2006/0280351 A1* | 12/2006 | Luping et al. | 382/128 |
| 2010/0172556 A1 | 7/2010 | Cohen et al. | |

OTHER PUBLICATIONS

M. Conti, "Finite Element Analysis of Self Expanding Braided Wirestent," Master's Thesis, Ghent University, 2007, 101 pages.*
I. Larrabide, et al, "Fast Virtual Deployment of Self Expandable Stents: Method and in Vitro Evaluation for Intracranial Aneurysmal Stenting," Medical Image Analysis, 2010, 10 pages.*
T. Ohyama, et al, "Development of Gold Stents for the Treatment of Intracranial Aneurysms: An Experimental Study in a Canine Model," American Journal of Neuroradiology, vol. 25, 2004, pp. 53 59.*
M. Villa Uriol, et al, "AngioLab: Integrated Technology for Patient Specific Management of Intracranial Aneurysms," 32nd Annual International Conference of the IEEE EMBS, Aug. 31 Sep. 4, 2010, pp. 6801-6804.*
M. Jedwab, et al, "Erratum—A Study of the Geometrical and Mechanical Properties of a Self-Expanding Metallic Stent—Theory and Experiment," Journal of Applied Biomaterials, vol. 5, 273, 1994, 1 page.*
CRC Standard Mathematical Tables 25th Edition, Ed. William H. Beyer, Chemical Rubber Company Press, 1973, p. 144.*
W. Wu, et al., "Delivery and Release of Nitinol Stent in Carotid Artery and Their Interactions: A Finite Element Analysis." Journal of Biomechanics 40, No. 13 (2007), pp. 3034-3040.*
F. Migliavacca, et al., "Stainless and Shape Memory Alloy Coronary Stents: A Computational Study on the Interaction With the Vascular Wall." Biomechanics and Modeling in Mechanobiology 2, No. 4, (2004), pp. 205-217.*
D. Liang, et al., "Finite Element Analysis of the Implantation of a Balloon Expandable Stent in Stenosed Artery," International Journal of Cardiology, vol. 104, 2005, pp. 314 318.*
F. Migliavacca, et al., "A Predictive Study of the Mechanical Behaviour of Coronary Stents by Computer Modelling," Medical Engineering and Physics, No. 27, (2005), pp. 13.*
Sadasivan, C. et al., "Numerical Investigation of Coll Configurations That Provide Untra-High Packing Density of Saccular Aneurysms", J Med Device (2009), vol. 3:4, pp. 1-15.
International Search Report dated Oct. 23, 2012 from International Patent Application No. PCT/US12/40964.

* cited by examiner

SYSTEM AND METHOD FOR SIMULATING DEPLOYMENT CONFIGURATION OF AN EXPANDABLE DEVICE

CROSS-REFERENCE TO RELATED APPLICATION(S)

This application claims priority to U.S. Provisional Patent Application No. 61/493,513, filed on Jun. 5, 2011, entitled "System and Method for Simulating Deployment Configuration of an Expandable Device," and U.S. Provisional Patent Application No. 61/493,976, filed on Jun. 6, 2011, entitled "System and Method for Simulating Deployment Configuration of an Expandable Device," each of which is herein incorporated by reference in its entirety.

FIELD OF INVENTION

The present invention relates generally to precision determination of and placement of a device in a cavity; and, more specifically, the present invention relates to simulating a deployment configuration of an expandable device, e.g., a braided device implant, in a tubular cavity.

INFORMATION

Various methods and devices are available to assist in the treatment of cavities in bodies and other locations. When dealing with a living body, such as a human or an animal, such methods and devices are critical to appropriately treating such cavities. For example, in the treatment of an aneurysm or other abnormality in a body vessel, one or more flow diverters may be used. Such flow diverters may include a braided flow diverter which involves a fine braided mesh. Such braided devices are compressed radially so that they may be inserted into delivery microcatheters for endovascular deployment within the blood vessels of the brain. When these devices are deployed or released from the catheter into the artery at the treatment site, they spontaneously re-expand (e.g., like a spring) until they contact the blood vessel wall. In their expanded form, these devices may assume a diameter which is 5 to 10 times greater than the radially compressed diameter. During this radial re-expansion, these braided devices foreshorten in the longitudinal direction. This foreshortening during deployment may be considerable and the devices may be at least two to three times longer within the microcatheter when they are radially compressed than when they are deployed within the parent artery. Once these devices are deployed, in general, they cannot be removed or re-positioned.

Proper aneurysm treatment requires very precise positioning of these devices within the parent artery. At present, such positioning by a physician is considered an art or learned technique. The deployed position is estimated subjectively by the physician based on the nominal diameter of the device, as well as the size and the configuration of the parent artery. This process is highly dependent on the level of the physician's experience, the deployment behavior of the particular flow diverter in use, and the complexity of the regional vascular anatomy. Further, even small errors in this process of estimation could lead to catastrophic procedural complications. Thus, physicians need to be able to predict with great accuracy the final exact length of a fully deployed flow diverting device before it is actually deployed.

Accordingly, there is a critical unmet need to be able to prospectively and accurately determine a deployed position of an expandable device to be applied to a tubular cavity. Further, such determinations need to be efficient enough to be applied within the context of clinical treatment.

SUMMARY

Embodiments of the present invention provide for a system, method, device, apparatus, and computer-readable medium having instructions thereon which when executed determine with precision the placement of a specific device in a cavity. Embodiments of the present invention provide for a system, method, device, apparatus, and computer-readable medium having instructions thereon which when executed simulate a deployed configuration of an expandable device, e.g., a flow diverter, in a cavity in a body. Embodiments of the present invention provide a prospective and accurate calculation of the deployed position of a braided expandable device in a tubular cavity in a body. Embodiments of the present invention provide a relationship, which may include one or more mathematical algorithms, executed by a processor which is based upon a method of laying helices along the luminal surface of the vessel with a pitch that continuously varies along the arterial axis according to the local circumference.

In embodiments of the present invention, an expandable device such as a flow diverter is used to treat various medical issues, including, for example, cerebral aneurysms. The accurate delivery and deployment of such an expandable device is critical to achieving adequate parent artery reconstruction. For example, a braided flow diverter—by virtue of its braided construction—can adapt to the local vessel or cavity geometry when released. That is, the braided configuration allows for good wall apposition because the angle between the device struts changes to adapt to changes in the vessel's diameter. However, as the braided flow diverter expands in diameter to adapt to the cavity geometry, the braided flow diverter shortens in length. Depending upon the cavity geometry, the shortening of the braided flow device can be significant, which provides a difficulty for determining what expandable device size is appropriate for the treatment and how to position the expandable device appropriately.

In embodiments of the present invention, a simulation of the to-be-deployed braided flow diverter or other expandable device is effected in order to determine the proper placement of the device to allow for the desired effect or result.

In embodiments of the present invention, a numerical-based simulation is provided which accurately simulates a deployed length of a device, e.g., a braided flow diverter, within a cavity, e.g., a vascular segment. In an embodiment, the simulation is based on three device parameters: diameter, length, and braiding angle. The braiding angle is the angle that the material or wires make with the device axis. A three-dimensional geometry of the vessel is obtained from the imaging. Such imaging may be, for example, a computed tomography (CT) scan or other image such as an magnetic resonance imaging (MRI) or ultrasound image. The three-dimensional geometry obtained includes, for example, the centerline and the lumen surface. In an embodiment, the distal vessel position at which deployment begins is known. Beginning at this location and moving proximally, a helix is constructed with the curved vessel centerline as its axis and with a varying pitch defined by the local vessel circumference. The total number of turns of a braided device remains conserved. In an embodiment, with a calculated pitch the total length of the vessel segment covered by the device can thus be calculated.

In embodiments of the present invention, a flow diverter of known diameter and braiding angle in air was cut to two different lengths (e.g., 2.5 cm and 4 cm), and deployed in three arbitrarily curved tubes. The vessel and device geometry were obtained by rotational angiography acquired with an Artis Zeego (manufactured by Siemens, Germany). The in-air device parameters were used to numerically simulate device deployment in the vessel geometry beginning at the same distal location as in the experiments. As a result, the rotational angiography reconstruction from one of the three trials and the simulated device configuration in the luminal geometry (in this situation, for example, only centerlines of every other wire pair are shown in the simulation), the absolute error between the experimentally measured and the numerically simulated deployed lengths was 1.1+/−0.1 mm (n=3); the percent error was 3.4+/−1.3%. Thus, in this embodiment, the results suggest that the deployed length of a flow diverter in any vessel segment can be calculated prior to deployment using the embodiments of the present invention. This information would assist neuro-interventionalists in determining device choice and vessel position at which device deployment should be initiated.

In embodiments of the present invention, by incorporating the expandable device's measurements as well as other measurements into the imaging software of any angiography system, an accurate visual rendering of the simulated deployed device can be presented to the physician before initiation of device deployment. The operator can then choose to reposition the delivery catheter, or re-size the device, based on this feedback to ensure accurate deployment. Incorporation of the numerical and device relationships defined by present invention into existing imaging system workstations can be done manageably. The determination of the relationships between the device and the vessel can be performed efficiently and the graphical information can be displayed three-dimensionally in real time according to embodiments of the present invention.

In embodiments of the present invention, the only inputs required for the algorithm are the nominal diameter, length and braiding angle (i.e., angle device wires to make the axis) of the device and the distal-most arterial point from where the deployment is to be initiated. The nominal device parameters are readily available from the manufacturers. The position of the distal tip of the delivery catheter dictates the deployment initiation point and can be precisely controlled during the fluoroscopically guided procedure.

In embodiments of the present invention, one can correlate and incorporate computational fluid dynamics simulations into imaging software such that the alterations in intra-aneurysmal hemodynamics due to the flow diverter can be calculated during treatment. Apart from calculating the deployed device position, the relationship management and/or algorithm can thus also be used to provide the detailed mesh configuration of the device in the region of the aneurysm neck for such simulations. In this embodiment, all that is required for this application is the additional input variable of number of wires within the braid of the flow diverter. Such parameter is also readily available from the manufacturers.

In embodiments of the present invention, the structural composition of a flow diverter makes it difficult for the treating physician to predict exactly where the proximal aspect of the device will land inside the artery once the physician released it into the artery, and so an algorithm has been developed which calculates the location of the device inside the artery before the physician or user begins to release it. This information can be displayed in a three dimensional and interactive format on a monitor screen already being used by the physician or other user during treatment. The user can use this to reevaluate or confirm the location at which the physician or user wants to begin releasing the device. The user can also use this to optimize device sizing.

Embodiments of the present invention provide for simulating placement of an expandable device in a tubular cavity, including: acquiring a three-dimensional image of a tubular cavity geometry; calculating a centerline of the tubular cavity; calculating a perimeter of the tubular cavity based on the centerline of the tubular cavity and the three-dimensional image of the tubular cavity geometry; calculating a length of a wire of the expandable device as the wire rotates along the perimeter of the tubular cavity in a deployment direction; determining a pitch of the rotation of the wire based on a local diameter at the centerline site of rotation and in-air parameters of the expandable device; and determining using a processor a deployed device length of the expandable device along the centerline of the tubular cavity.

Embodiments of the present invention include verifying the accuracy of the configuration of the expandable device based on a comparison of the calculated wire length and a known wire length.

Embodiments of the present invention include determining the centerline of the tubular cavity from an image scan of a region of interest of the tubular cavity that may include abnormalities.

Embodiments of the present invention include calculating the wire length for each increment along a deployment direction commences at an initial input point on the wall of the tubular cavity. Embodiments of the present invention include providing the initial input point by at least one of a manual entry input and an automatic entry input via the processor.

Embodiments of the present invention include calculating the deployed device length of the expandable device is effected such that the summation of each wire length increment is equal to the total length of the wires.

Embodiments of the present invention include determining the total length of the wires as a function of in-air parameters of the expandable device including a width, a braiding angle, and a device diameter of the expandable device.

Embodiments of the present invention include that the expandable device is a braided intravascular implant.

Embodiments of the present invention provide a device, method and system for accurately predicting a proximal landing point of one or more deployed flow diverters or the like, as well as the configuration of each wire or positioning device.

Embodiments of the present invention provide for a processor or machine to execute one or more of the steps or features of each respective embodiment.

The term physician is used herein to refer to a user of an embodiment of the present invention for example purposes. Embodiments of the present invention are referred to being used to treat a medical condition of a patient. However, the present invention is not limited to such uses and instead is applicable in calculating precise positioning in a variety of fields and industries including fluid dynamics, etc.

DETAILED DESCRIPTION

Embodiments of the present invention provide for a systematic approach to the care, diagnosis, and subsequent treatment of a patient.

Embodiments of the present invention provide for a systematic approach to the relatively accurate prediction of the placement of a flow diverter and its placement device.

Figure 1A:
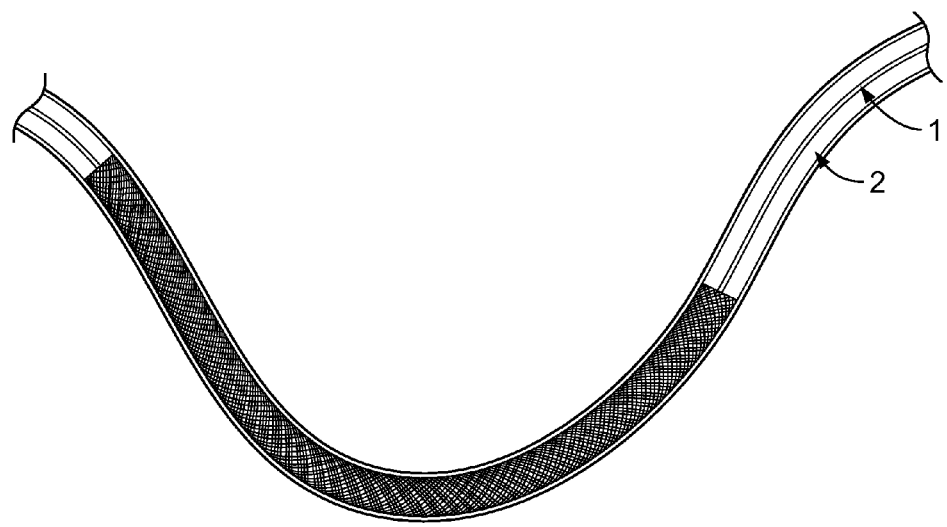
FIG. 1A shows a deployed braided expandable device inside a cavity or tubular cavity.
Figure 1B:
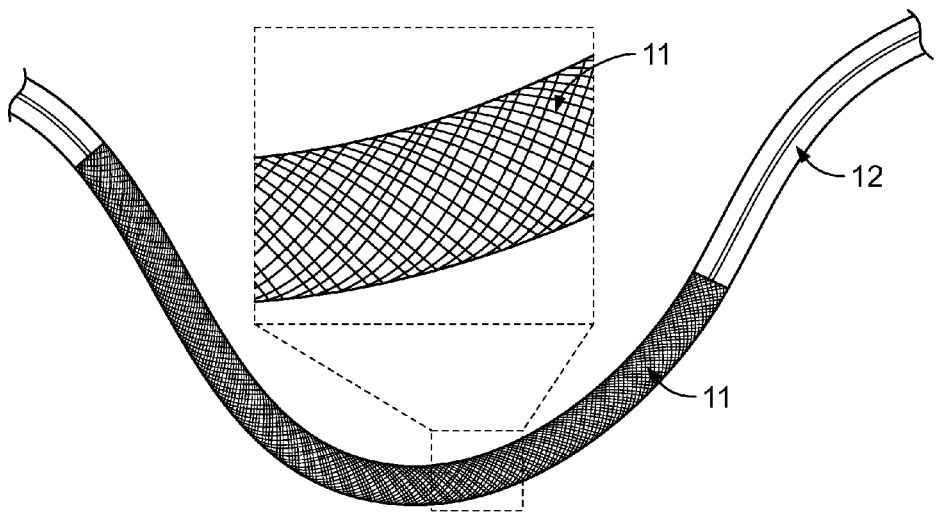
FIG. 1B shows a simulation of the deployed braided expandable device of FIG. 1A according to an embodiment of the present invention.

In FIGS. 1A and 1B, an experiment is shown which illustrates some components of an embodiment of the present invention. For example, FIG. 1A shows in vitro experimental data image showing the location of a deployed braided expandable device 1 inside a curved tubular cavity 2. FIG. 1B shows a simulation of the configuration of the deployed braided expandable device 11 in a similar curved tubular cavity 12 of FIG. 1A. In embodiments of the present invention, knowledge of the length of the tubular cavity—among other data—is needed to determine the type and size of the expandable device to use. From the FIG. 1A image, the simulation of the length of the tubular cavity was possible.

In embodiments of the present invention, dimensional images of a specific cavity region of interest can be obtained from an imaging system including at least one of magnetic resonance imaging (MRI), nuclear magnetic resonance imaging (NMR), computed tomography (CT), positron emission tomography (PET), single-photon emission computed tomography (SPECT), ultrasound, photoacoustic imaging, and radiography. In embodiments of the present invention, three-dimensional images of a cavity are used to determine a region of interest, including the length of the region of interest.

Figure 2:
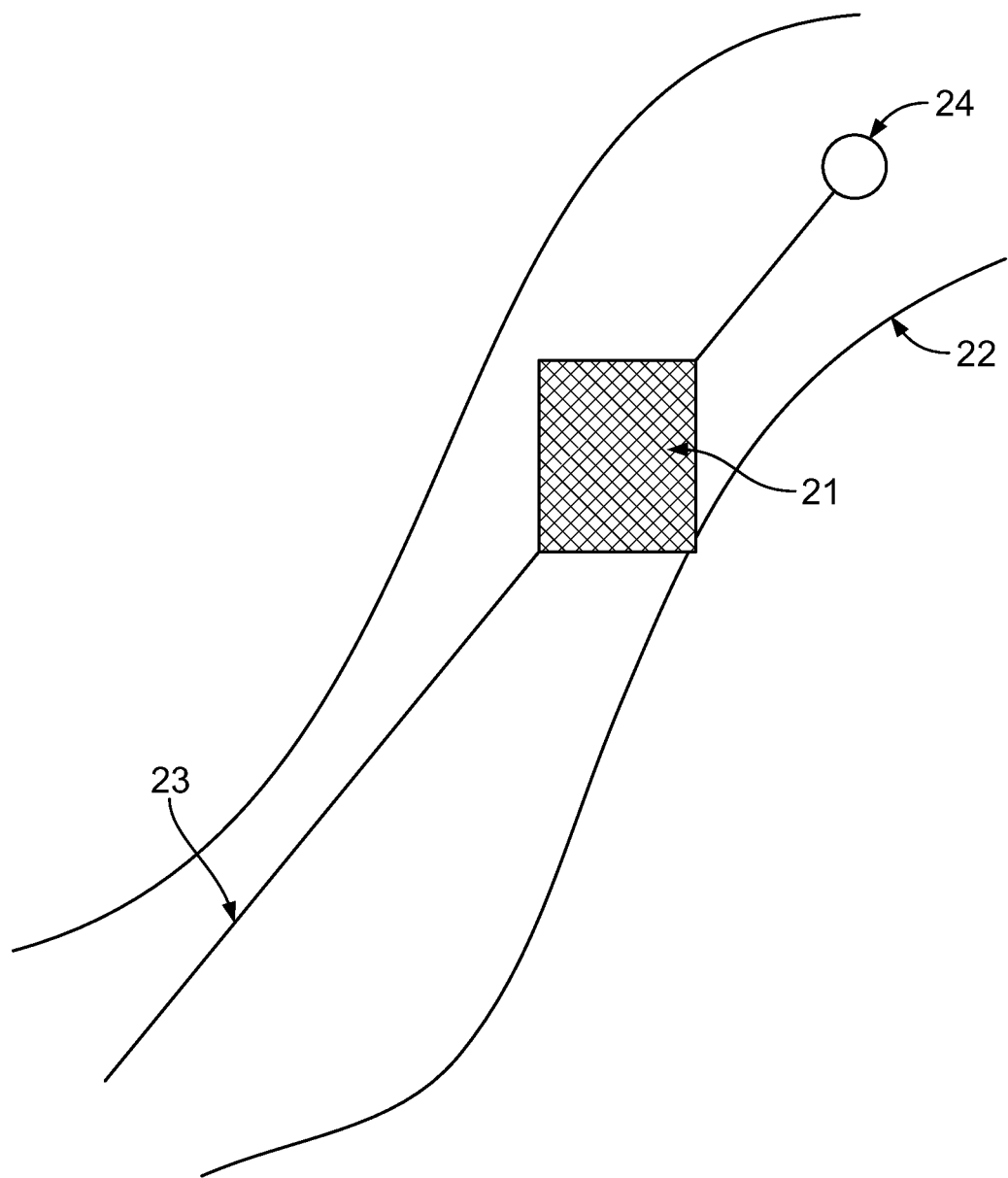
FIG. 2 shows an expandable device to be deployed in a cavity or tubular cavity according to an embodiment of the present invention.

FIG. 2 shows an expandable device 21 to be deployed in a tubular cavity according to an embodiment of the present invention. In practice, an expandable device 21 within a tube 25 is introduced into a tubular cavity 22, e.g., a vascular cavity. A pusher wire 23 is used to navigate the system of the expandable device 21 and the tube 25 up through the tubular cavity 22 to a region of interest or location for deployment of the expandable device 25. The pusher wire 23 includes a distal marker 24. The distal marker 24 is viewable on a image scan, and when the distal marker 24 reaches the deploying region, that distal marker 24 effectively indicates where the distal end of the to-be-deployed expandable device 21 will be. In embodiments of the present invention, a simulation of such a region of interest, including an example expandable device, is made so that an accurate estimation of where the proximal end of the expandable device will land for a given distal end location is obtained.

Figure 3:
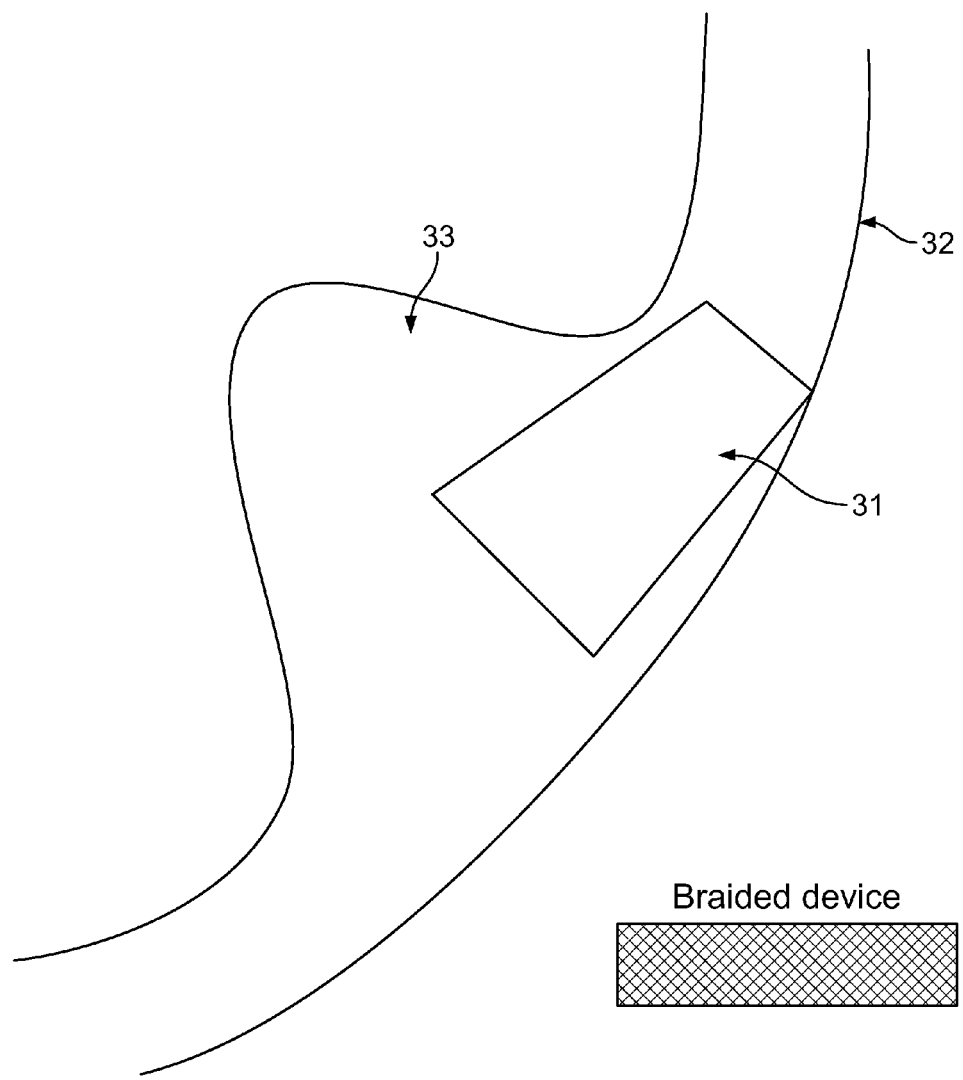
FIG. 3 shows a simulation of a deployed expandable device in a cavity or tubular cavity according to an embodiment of the present invention.

FIG. 3 shows a simulation of a deployed expandable device in a tubular cavity according to an embodiment of the present invention. When a physician is placing a flow diverter in a blood vessel in a cranial cavity, it may be dangerous, if not impossible, to remove a flow diverter which has been placed improperly. The walls of the blood vessel in the brain region are thin, fragile, and tend to be windy or curvy in their paths. Accordingly, embodiments of the present invention can be used to simulate such areas based on a multi-dimensional image scan and other known or calculated data. In such cases, as shown in FIG. 3, simulation of a expandable device 31 in a tubular cavity such as a blood vessel 32 can assist greatly in determining whether a deployed expandable device 31 is of a proper length and fit. As shown in FIG. 3, the expandable device 31 is too short to cover the region of interest in the blood vessel 32. Here, an aneurysm or other abnormality 33 is a part of the region of interest. In practice, if the expandable device 31 is too short, then one or more additional expandable devices will need to be deployed properly and accurately in the same region of interest. There are several dangers to this technique, as well as excessive cost per treatment. With embodiments of the present invention, one can simulate the region and the expandable device to determine that the expandable device is a proper fit, or at least know in advance if multiple expandable devices will be needed to treat a specific region of interest.

Figure 4:
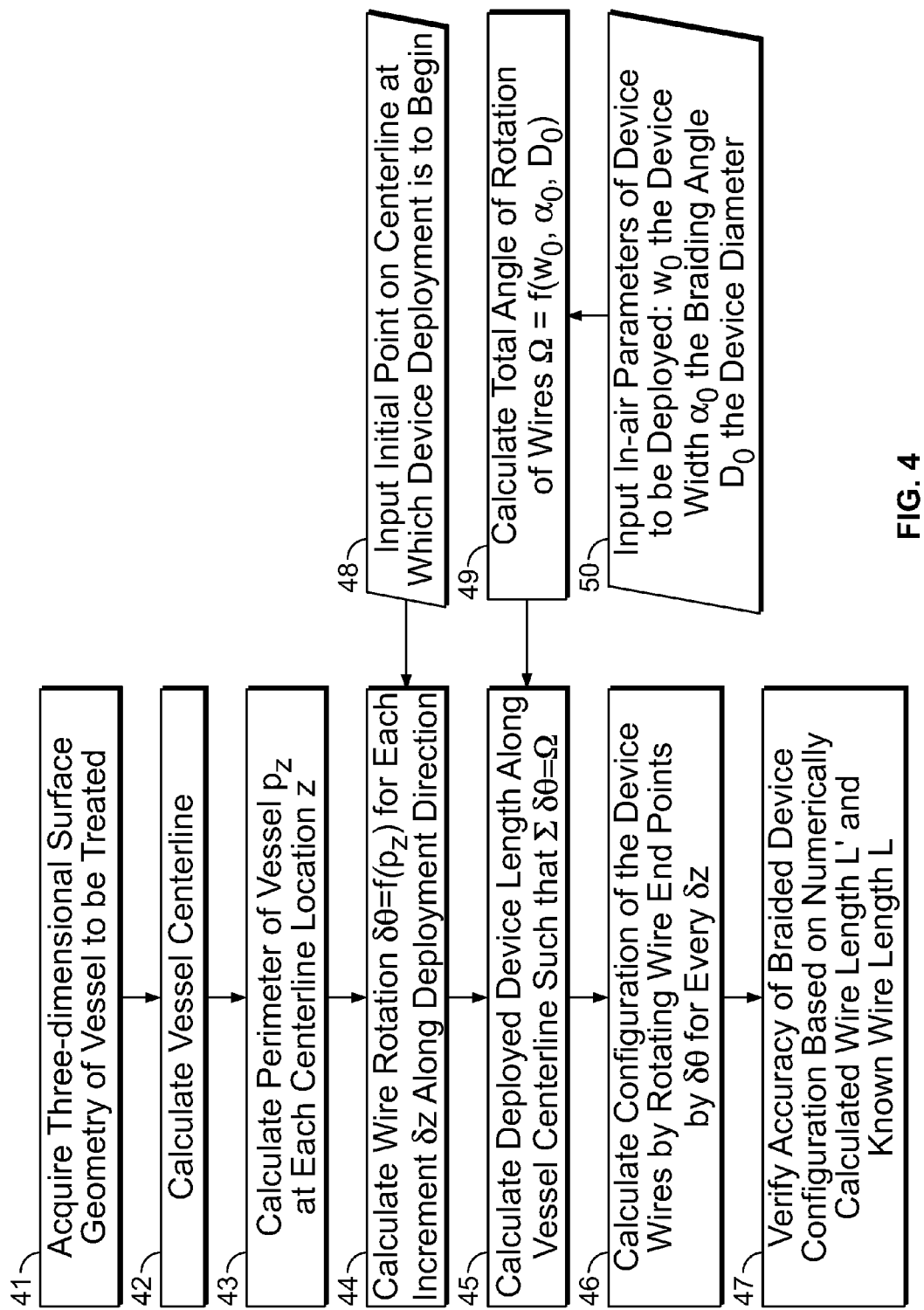
FIG. 4 shows a flowchart illustrating an embodiment of the present invention.

In FIG. 4, a flowchart illustrating an embodiment of the present invention is shown. In an embodiment of the present invention, a simulation of the placement of an expandable device in a tubular cavity is made by the following method and system. A three-dimensional image of a tubular cavity geometry or three-dimensional surface geometry of a cavity to be treated is acquired 41. For example, a three-dimensional CT or MRI image is obtained, from which a region of interest or cavity is identified. A centerline of the cavity is calculated 42. For example, the centerline of the cavity is determined from the image scan of a region of interest which may include an abnormality. For example, such an abnormality is an aneurysm. A perimeter of the cavity based on the centerline of the tubular cavity and the three-dimensional image of the tubular cavity geometry is calculated 43. The perimeter $p_z$ of the vessel is calculated at each centerline location z. The length of a wire of the expandable device as the wire rotates along the perimeter of the tubular cavity in a deployment direction is calculated. For example, an initial point on the centerline at which the device deployment is to begin is inputted 48 into a processor. For example, the wire length calculation for each increment along a deployment direction commences at an initial input point on the wall of the cavity. The initial point is entered manually to the processor and/or automatically entered in the processor. The automatic entering of the initial point to the processor may be via a software module that identifies a luminous region or abnormal-shaped section of a cavity on an image or software-representation of an image.

In FIG. 4, the wire rotation $\delta\theta=f(p_z)$ is calculated for each increment $\delta z$ along the deployment direction 44. A pitch of the rotation of the wire based on a local diameter at the centerline site of rotation and in-air parameters of the expandable device is determined. The total angle of rotation of wires $\Omega=f(w_0, \alpha_0, D_0)$ is calculated, where the in-air parameters of the device to be deployed are: the device width $w_0$, the braiding angle $\alpha_0$ of the device, and the device diameter $D_0$ 50. The deployed device length along the cavity centerline is calculated such that $\Sigma\delta\theta=\Omega$ 45. The configuration of the wires of the device to be deployed may be calculated by rotating the wire endpoints by $\delta\theta$ for every $\delta z$ 46. In an embodiment, the accuracy of the braided device configuration is verified based on comparing the calculated wire length and the known wire length of the device to be deployed 47.

In embodiments of the present invention, given the vessel surface geometry and the distal point at which device deployment begins, a deployed length of the deployed device in the vessel is determined by varying the pitch of the positioning wires with the local vessel circumference. For example, a centerline of the vessel geometry provides an estimated length of flow diverter device to employ. The distal point at which deployment begins is obtained from the fluoroscopy image of the microcatheter tip (i.e., a positioning wire). The deployed device location is then determined and displayed. The distal point of deployment initiation can then be corrected prior to actual deployment based on the simulation of the deployment.

In embodiments of the present invention, an expandable device may be one or more of the following: a braided device, a braided expandable device, a braided intravascular implant, an expanding braided intravascular implant, a self-expanding braided device, and a self-expanding braided flow diverter.

In embodiments of the present invention, a tubular cavity or region of interest may be one or more of the following: a vascular cavity, a blood vessel, a blood vessel in a cranial cavity, a bile duct cavity, a urinary tract cavity, an intestine cavity, and a tracheal cavity, of a body. In embodiments of the present invention, a tubular cavity or region of interest may be in one or more of the following: a cranial cavity, a thoracic cavity, a diaphragm cavity, an abdominal cavity, a pelvic cavity, a pericardial cavity, a pleural cavity, and a vertebral cavity, of a body.

In embodiments of the present invention, the multi- or three-dimensional image is obtained from an imaging system including at least one of magnetic resonance imaging (MRI), nuclear magnetic resonance imaging (NMR), computed tomography (CT), positron emission tomography (PET), single-photon emission computed tomography (SPECT), ultrasound, photoacoustic imaging, and radiography.

Embodiments of the present invention may be used in non-medical industries and/or with non-live bodies. Multiple devices or flow diverters may be simulated for deployment using embodiments of the present invention.

In embodiments of the present invention, a non-transitive medium or computer-readable storage medium having instructions thereon to execute one or more embodiments of the present invention or system can be run on a variety of processors, including handheld processor(s), electronic notepad(s), personal computer(s), mobile telephone(s), mobile device(s), portable processor(s), mainframe processor(s), etc. Such storage mediums may also include one or more of: server, processor, chip, smartcard, flash memory, portable storage drive, and non-portable storage drive. Embodiments of the present invention are platform independent, and can be executed on a variety of operating systems.

It should be understood that there exist implementations of other variations and modifications of the invention and its various aspects, as may be readily apparent to those of ordinary skill in the art, and that the invention is not limited by specific embodiments described herein. The features and embodiments—including their individual features therein—described above are combinable with and without each other. It is therefore contemplated that the present invention covers any and all modifications, variations, combinations and/or equivalents that fall within the scope of the basic underlying principals disclosed and claimed herein.

What is claimed is:

1. A computer-implemented method, comprising:
   acquiring, by a computer processor, a three-dimensional image of a tubular cavity;
   calculating, by the processor, a centerline of the tubular cavity;
   for each of a plurality of positions along a length of the tubular cavity, calculating, by the processor and based on the three-dimensional image and the centerline of the tubular cavity, a respective value of a perimeter of the tubular cavity at the respective position, wherein the values of the perimeter calculated for the plurality of positions vary;
   based at least on the calculated perimeter values, calculating, by the processor and for each of a plurality of deployment increments between respective pairs of the plurality of positions along the length of the tubular cavity, a respective angle of rotation of a wire of an expandable device as the wire rotates within the respective deployment increment along the perimeter of the tubular cavity and in a deployment direction;
   obtaining, by the processor, a total in-air angle of rotation of the wire over an entire length of the expandable device;
   identifying, by the processor, a sequential subset of the plurality of deployment increments whose corresponding calculated angles of rotation in combination equal the obtained total in-air angle of the rotation of the wire;
   outputting, by the processor, a length of the identified sequential subset of the plurality of deployment increments as an estimate for how long, geometrically, the expandable device will be when the expandable device is subsequently deployed in the tubular cavity; and
   displaying of a graphical component representing the expandable device relative to a representation corresponding to the three-dimensional image.

2. The method of claim 1, further comprising:
   verifying an accuracy of the estimate based on a comparison of a total of wire lengths, as the wire rotates along the perimeter within the identified sequential subset of the plurality of deployment increments, and a known wire length.

3. The method of claim 1, wherein the three-dimensional image includes or is based on an image scan of a region of interest of the tubular cavity determined to be at risk for abnormalities, from which image scan the centerline of the tubular cavity is determined.

4. The method of claim 1, wherein the calculating of the respective angles of rotation of the wire for the respective plurality of deployment increments commences at an initial input point on a wall of the tubular cavity and continues along the deployment direction.

5. The method of claim 4, wherein the initial input point is provided by at least one of a manual entry input and an automatic entry input via the processor.

6. The method of claim 1, wherein the expandable device is at least one of a braided device, a self-expanding braided device, an expanding braided intravascular implant, and a self-expanding braided flow diverter.

7. The method of claim 1, wherein the tubular cavity is at least one of a vascular cavity, a blood vessel, a blood vessel in a cranial cavity, a bile duct cavity, a urinary tract cavity, an intestine cavity, and a tracheal cavity, in a human body.

8. The method of claim 1, wherein the three-dimensional image is obtained from an imaging system including at least one of magnetic resonance imaging (MRI), nuclear magnetic resonance imaging (NMR), computed tomography (CT), positron emission tomography (PET), single-photon emission computed tomography (SPECT), ultrasound, photoacoustic imaging, and radiography.

9. The method of claim 1, wherein the obtaining of the total in-air angle of rotation of the wire includes determining the total in-air angle of rotation over the entire length of the expandable device based on in-air parameters of the expandable device.

10. The method of claim 9, wherein the respective angles of rotation calculated for the respective deployment increments is calculated further based on the in-air parameters.

11. The method of claim 9, further comprising calculating, for each of the plurality of deployment increments, a respective pitch of the wire as the wire rotates within the respective deployment increment along the perimeter of the tubular cavity and in a deployment direction, wherein the calculation of the angles of rotation is based on the calculated pitches and the calculation of the respective pitches is based on respective local diameters of the tubular cavity within the respective deployment increments and on the in-air parameters of the expandable device.

12. The method of claim 9, wherein the in-air parameters of the expandable device include the length, a braiding angle, and a device diameter of the expandable device.

13. The method of claim 12, wherein the expandable device is a braided intravascular implant.

14. The method of claim 1, further comprising calculating, for each of the plurality of deployment increments, a respective pitch of the wire as the wire rotates within the respective deployment increment along the perimeter of the tubular cavity and in a deployment direction, wherein the calculation of the angles of rotation is based on the calculated pitches.

15. A system, comprising:
processing circuitry;
an interface; and
an output device;
wherein the processing circuitry is configured to:
acquire, via the interface, a three-dimensional image of a tubular cavity;
calculate a centerline of the tubular cavity;
for each of a plurality of positions along a length of the tubular cavity, calculate, based on the three-dimensional image and the centerline of the tubular cavity, a respective value of a perimeter of the tubular cavity at the respective position, wherein the values of the perimeter calculated for the plurality of positions vary;
based at least on the calculated perimeter values, calculate, for each of a plurality of deployment increments between respective pairs of the plurality of positions along the length of the tubular cavity, a respective angle of rotation of a wire of an expandable device as the wire rotates within the respective deployment increment along the perimeter of the tubular cavity and in a deployment direction;
obtain a total in-air angle of rotation of the wire over an entire length of the expandable device;
identify a sequential subset of the plurality of deployment increments whose corresponding calculated angles of rotation in combination equal the obtained total in-air angle of the rotation of the wire;
output via the output device a length of the identified sequential subset of the plurality of deployment increments as an estimate for how long, geometrically, the expandable device will be when the expandable device is subsequently deployed in the tubular cavity; and
display via the output device a graphical component representing the expandable device relative to a representation corresponding to the three-dimensional image.

16. The system of claim 15, wherein the processor is configured to verify an accuracy of the estimate based on a comparison of a total of wire lengths, as the wire rotates along the perimeter within the determined number identified sequential subset of the plurality of deployment increments, and a known wire length.

17. The system of claim 15, wherein the three-dimensional image includes or is based on an image scan of a region of interest of the tubular cavity determined to be at risk for abnormalities, from which image scan the centerline of the tubular cavity is determined.

18. The system of claim 15, wherein the calculation of the respective angles of rotation of the wire for the respective plurality of deployment increments commences at an initial input point on a wall of the tubular cavity and continues along the deployment direction.

19. The system of claim 18, wherein the initial input point is provided by at least one of a manual entry input and an automatic entry input via the processor.

20. The system of claim 15, wherein the total in-air angle of rotation of the wire over the entire length of the expandable device is obtained by determining the total in-air angle of rotation based on in-air parameters of the expandable device, the in-air parameters including the length, a braiding angle, and a device diameter of the expandable device.

21. The system of claim 20, wherein the expandable device is a braided intravascular implant.

22. The system of claim 15, wherein the expandable device is at least one of a braided device, a self-expanding braided device, an expanding braided intravascular implant, and a self-expanding braided flow diverter.

23. The system of claim 15, wherein the tubular cavity is at least one of a vascular cavity, a blood vessel, a blood vessel in a cranial cavity, a bile duct cavity, a urinary tract cavity, an intestine cavity, and a tracheal cavity, in a human body.

24. The system of claim 15, wherein the three-dimensional image is obtained from an imaging system including at least one of magnetic resonance imaging (MRI), nuclear magnetic resonance imaging (NIVIR), computed tomography (CT), positron emission tomography (PET), single-photon emission computed tomography (SPECT), ultrasound, photoacoustic imaging, and radiography.

25. A non-transitory machine-readable storage medium on which are stored instructions that are executable by a processor and that, when executed by the processor, cause the processor to execute a method, the method comprising:
calculating a centerline of the tubular cavity;
for each of a plurality of positions along a length of a tubular cavity, calculating, based on a three-dimensional image and the centerline of the tubular cavity, a respective value of a perimeter of the tubular cavity at the respective position, wherein the values of the perimeter calculated for the plurality of positions vary;
based at least on the calculated perimeter values, calculating, for each of a plurality of deployment increments between respective pairs of the plurality of positions along the length of the tubular cavity, a respective angle of rotation of a wire of an expandable device as the wire rotates within the respective deployment increment along the perimeter of the tubular cavity and in a deployment direction;

obtaining a total in-air angle of rotation of the wire over an entire length of the expandable device;

identifying a sequential subset of the plurality of deployment increments whose corresponding calculated angles of rotation in combination equal the obtained total in-air angle of the rotation of the wire;

outputting a length of the identified sequential subset of the plurality of deployment increments as an estimate for how long, geometrically, the expandable device will be when the expandable device is subsequently deployed in the tubular cavity; and displaying of a graphical component representing the expandable device relative to a representation corresponding to the three-dimensional image.

26. The medium of claim 25, wherein the method further comprises:

verifying an accuracy of the estimate based on a comparison of a total of the wire length, as the wire rotates along the perimeter within the identified sequential subset of the plurality of deployment increments, and a known wire length.

27. The medium of claim 25, wherein the three-dimensional image includes or is based on an image scan of a region of interest of the tubular cavity determined to be at risk for abnormalities, from which image scan the centerline of the tubular cavity is determined.

28. The medium of claim 25, wherein the calculating of the respective angles of rotation of the wire for the respective plurality of deployment increments commences at an initial input point on a wall of the tubular cavity and continues along the deployment direction.

29. The medium of claim 28, wherein the initial input point is provided by at least one of a manual entry input and an automatic entry input via the processor.

30. The medium of claim 25, wherein the obtaining of the total in-air angle of rotation includes determining the total in-air angle of rotation based on in-air parameters of the expandable device that include the length, a braiding angle, and a device diameter of the expandable device.

31. The medium of claim 30, wherein the expandable device is a braided intravascular implant.

32. The medium of claim 25, wherein the expandable device is at least one of a braided device, a self-expanding braided device, an expanding braided intravascular implant, and a self-expanding braided flow diverter.

33. The medium of claim 25, wherein the tubular cavity is at least one of a vascular cavity, a blood vessel, a blood vessel in a cranial cavity, a bile duct cavity, a urinary tract cavity, an intestine cavity, and a tracheal cavity, in a human body.

34. The medium of claim 25, wherein the three-dimensional image is obtained from an imaging system including at least one of magnetic resonance imaging (MRI), nuclear magnetic resonance imaging (NMR), computed tomography (CT), positron emission tomography (PET), single-photon emission computed tomography (SPECT), ultrasound, photoacoustic imaging, and radiography.

35. A computer-implemented method for, prior to deployment of an expandable device into a deployed state in a tubular cavity, providing an estimate of how long geometrically, the expandable device will be in the deployed state, the method comprising:

processing, by a computer processor, an image of the tubular cavity, wherein a perimeter of the tubular cavity varies over a length of the tubular cavity;

obtaining, by the processor, a total in-air pitch or total angle of rotation of a wire over an entire length of the expandable device;

determining, by the processor and as the estimate, a length of a segment in the tubular cavity in which an angle of rotation of the wire, when rotated along the perimeter of the tubular cavity, equals the obtained total in-air angle of rotation, wherein the angle of rotation, when rotated along the perimeter of the tubular cavity, is determined at least based on the processed image of the tubular cavity:

outputting, by the processor, the determined estimate as a graphical component relative to a representation corresponding to the image; and displaying of the graphical component relative to the representation corresponding to the image.

36. The method of claim 35, wherein the obtaining of the total in-air angle of rotation includes determining the total in-air angle of rotation based on in-air parameters of the expandable device, and the determination of the angle of rotation when rotated along the perimeter of the tubular cavity is further based on the in-air parameters.

37. The method of claim 36, wherein the in-air parameters include the length of the expandable device, a braiding angle of the expandable device, and a diameter of the expandable device.

38. A computer-implemented method for, prior to deployment of an expandable device into a deployed state in a tubular cavity, providing an estimate of how long, geometrically, the expandable device will be in the deployed state, the method comprising:

processing, by a computer processor, an image of the tubular cavity, wherein a perimeter of the tubular cavity varies over a length of the tubular cavity;

obtaining, by the processor, a total in-air length of a wire of the expandable device as the wire helically rotates over an entire in-air length of the expandable device; and determining, by the processor and as the estimate, a length of a segment in the tubular cavity in which a length of the wire, when rotated along the perimeter of the tubular cavity, equals the obtained total in-air length, wherein the length of the wire in the segment is determined at least based on the processed image of the tubular cavity;

outputting, by the processor, the determined estimate as a graphical component relative to a representation corresponding to the image; and displaying of the graphical component relative to the representation corresponding to the image.

39. A computer-implemented method, comprising:
acquiring, by a computer processor, a three-dimensional image of a tubular cavity;

calculating, by the processor, a centerline of the tubular cavity;

for each of a plurality of positions along a length of the tubular cavity, calculating, by the processor and based on the three-dimensional image and the centerline of the tubular cavity, a respective value of a perimeter of the tubular cavity at the respective position, wherein the values of the perimeter calculated for the plurality of positions vary;

based at least on the calculated perimeter values, calculating, by the processor and for each of a plurality of deployment increments between respective pairs of the plurality of positions along the length of the tubular cavity, a respective value quantifying a helical property of a wire of an expandable device as the wire rotates within the respective deployment increment along the perimeter of the tubular cavity and in a deployment direction;

obtaining, by the processor, a total in-air value quantifying the helical property of the wire over an entire length of the expandable device;

identifying, by the processor, a sequential subset of the plurality of deployment increments whose corresponding calculated values quantifying the helical property in combination equal the determined total in-air value quantifying the helical property of the wire;

outputting, by the processor, a length of the identified sequential subset of the plurality of deployment increments as an estimate for how long, geometrically, the expandable device will be when the expandable device is subsequently deployed in the tubular cavity; and displaying of a graphical component representing the expandable device relative to a representation corresponding to the three-dimensional image.

* * * * *